United States Patent
Forman et al.

(10) Patent No.: US 7,571,728 B2
(45) Date of Patent: Aug. 11, 2009

(54) GROSS PATHOLOGY BREAST MAP

(75) Inventors: Michael R. Forman, Los Gatos, CA (US); Darius Francescatti, Barrington, IL (US)

(73) Assignee: Xoft, Inc., Sunnyvale, CA (US)

( * ) Notice: Subject to any disclaimer, the term of this patent is extended or adjusted under 35 U.S.C. 154(b) by 745 days.

(21) Appl. No.: 10/820,433

(22) Filed: Apr. 8, 2004

(65) Prior Publication Data
US 2005/0011526 A1    Jan. 20, 2005

Related U.S. Application Data

(60) Provisional application No. 60/461,433, filed on Apr. 10, 2003.

(51) Int. Cl.
*A61B 19/00* (2006.01)
(52) U.S. Cl. .................................. 128/897
(58) Field of Classification Search ............. 128/897, 128/898; 600/300, 549, 407, 587; 434/267; 424/445; 428/36.1; 602/41–57
See application file for complete search history.

(56) References Cited

U.S. PATENT DOCUMENTS 4,181,859 A  *  1/1980  Vitalini ..................... 378/164
5,002,735 A  *  3/1991  Alberhasky et al. ........... 422/99
5,020,088 A      5/1991  Tobin
5,156,150 A    10/1992  Lary
D348,618 S   *  7/1994  Leslie et al. ................. D10/64
5,383,234 A     1/1995  Russell
5,913,686 A  *  6/1999  VanWinkle ................. 434/267
6,714,628 B2    3/2004  Broyles et al.

* cited by examiner

*Primary Examiner*—Samuel G Gilbert
(74) *Attorney, Agent, or Firm*—Thomas M. Freiburger

(57) ABSTRACT

A system and method to position and orient an excised breast tissue specimen on a support structure in a duplicate anatomic orientation relative to the operated breast is provided. One embodiment of the system includes an anatomically representative map of the breast under investigation. The system allows a surgeon to suture, ink, or otherwise fix the excised specimen on the map in accordance to its original position and orientation in the operated breast or organ. A radiogram of the excised specimen can be taken that shows the location of calcifications on a grid with radiopaque markers. The system allows a pathologist to cut through the specimen utilizing the map as a template in order to perform histological analysis and correlate the position and orientation of each slice to its anatomic position in the breast and thereby direct a precise and anatomically accurate re-excision by the surgeon if so required.

5 Claims, 6 Drawing Sheets

GROSS PATHOLOGY BREAST MAP

RELATED APPLICATION DATA

This application claims priority under 35 U.S.C. § 119 to U.S. Provisional Patent Application Ser. No. 60/461,433 filed Apr. 10, 2003, the disclosure of which is incorporated in its entirety herein by reference.

BACKGROUND OF THE INVENTION

1. Field of the Invention

The present invention relates generally to the field of surgery and pathology. In one embodiment, the invention includes devices and methods for positioning and orienting excised tissue specimens with a support structure. The support structure generally illustrates the position of the excised tissue specimen with respect to the tissue from which it was excised.

2. Description of the Related Art

Technology available today generally utilizes radiologically placed markers to identify a radiographically identifiable breast abnormality within an excised tissue specimen. However, such technology generally fails to accurately identify the correct anatomical relationship of the excised specimen margins with the actual surgical cavity created by tissue removal. Radiographic localization is utilized solely to identify an area for diagnosis. In particular, within the field of breast surgery, there exists no standardized method of orienting excised breast biopsy or lumpectomy (cancer) specimens whether radiographically or non-radiographically (i.e., by palpation or ultrasound identified abnormalities vis-à-vis the operative site).

SUMMARY OF THE INVENTION

In one embodiment, a gross pathology breast map system for examining a breast tissue specimen while recording and maintaining an anatomical location of the specimen to a breast from which it was excised is provided. The system includes a top layer and a second layer. The top layer includes a substantially hard, suturable, tackable material, and a graphic representation of a breast anatomy. The graphic representation illustrates a nipple located inside an outline of the breast, an axilla, and an alpha-numeric background grid to define a location of the specimen on the gross pathology breast map system.

The second layer is affixed and aligned to the top layer and is made of an absorptive, suturable, tackable material. The second layer has a back surface that includes radio-opaque elements that correspond to the graphic representation of the top layer.

In another embodiment of the present invention a gross pathology breast map system for examining a breast tissue specimen while recording and maintaining an anatomical location of the specimen to the breast from which it was excised is provided. The system includes a top layer, a second layer, and a third layer.

The top layer is made of a substantially hard, suturable, tackable material, and includes a graphic representation of a breast anatomy. The graphic representation shows a nipple located inside an outline of the breast, an axilla, and an alpha-numeric background grid to define a location of the specimen on the map.

The second layer is affixed and aligned to the top layer, and includes an absorptive, suturable, tackable material. The third layer is affixed to and aligned with the second layer. The third layer includes radio-opaque markers that correspond to the graphic representation of the top layer.

In another embodiment of the present invention, a method for radiographically and histologically examining a breast tissue specimen while recording and maintaining the an anatomical location of the specimen to the breast from which it was excised is provided. The method includes the step of excising a tissue specimen from a breast location in a breast and affixing the tissue specimen on a gross pathology breast map in a map location that is substantially the same as the breast location. The method further includes the steps of placing the gross pathology breast map with affixed specimen into a leakproof, resealable container, taking a radiographic image of the specimen, and submitting the gross pathology breast map with affixed specimen for pathologic sectioning.

In yet another embodiment of the present invention, a gross pathology breast map system for examining a breast tissue specimen while recording and maintaining the an anatomical location of the specimen to the breast from which it was excised is provided. The system includes a top layer, a second layer, and a third layer.

The top layer is made of a substantially hard, suturable, tackable material. The top layer has a graphic representation of a breast anatomy which shows a nipple located inside an outline of the breast, an axilla, and an alpha-numeric background grid to define a location of the specimen on the map.

The second layer is affixed and aligned to the top layer. The second layer includes an absorptive, suturable, tackable material. The second layer also has a back surface that includes radio-opaque markers that correspond to the graphic representation of the top layer.

The third, detachable, radiosensitive bottom layer is affixed and aligned to the second layer. The third layer includes a second graphical representation of the breast that is aligned to the graphic representation of the top layer.

In another embodiment, a method for radiographically and histologically examining a breast tissue specimen while recording and maintaining an anatomical location of the specimen to the breast from which it was excised is provided. The method includes the steps of excising a tissue specimen from a breast location in a breast of a patient and identifying margins of the tissue specimen. The method also includes the steps of affixing the tissue specimen on a gross pathology breast map in a representative location that is substantially representative of the breast location, placing the gross pathology breast map with affixed specimen into a leakproof, resealable container, and taking a radiographic image of the specimen. The method also includes removing a radiosensitive back layer from the gross pathology breast map and including it in a patient's chart, and providing the gross pathology breast map with affixed specimen for pathologic sectioning.

In yet another embodiment of the present invention, a radiographic and histologic kit for examining a breast tissue specimen while recording and maintaining an anatomical location of the specimen to the breast from which it was excised is provided. The kit includes a gross pathology breast map; at least one marker selected from the group comprising colored inks, colored sutures, and colored staples; and a resealable, leakproof container.

DETAILED DESCRIPTION OF THE PREFERRED EMBODIMENT

Figure 1:
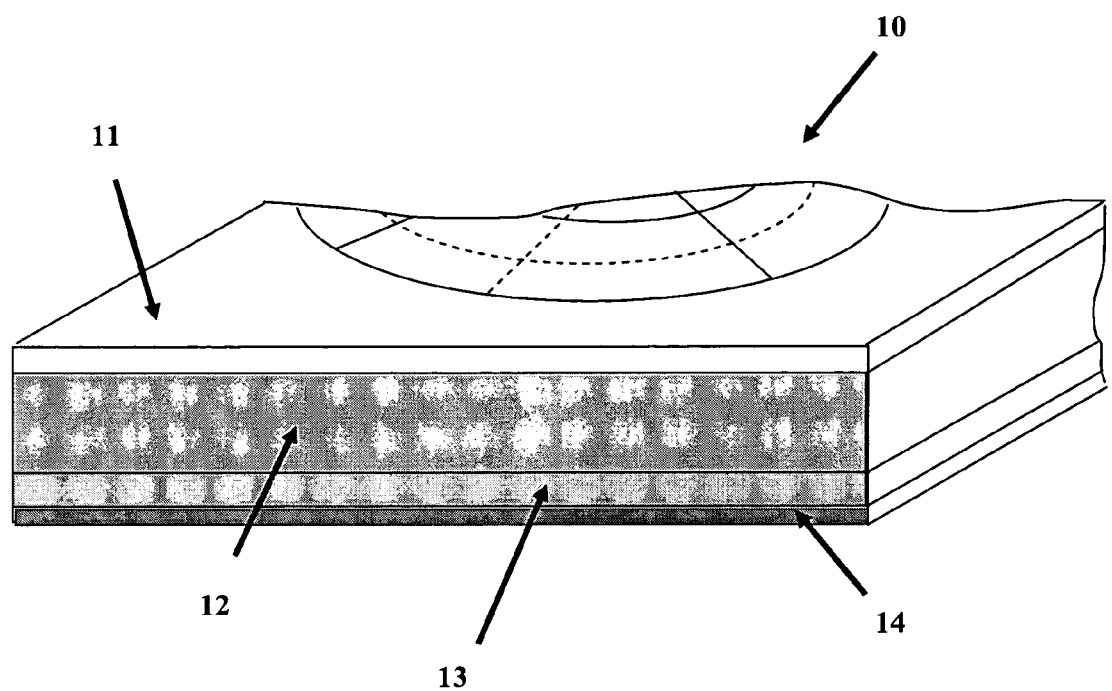
FIG. 1 illustrates a cross-sectional view of one embodiment of a breast map device including its layers.

One embodiment of the present invention allows positioning and orientation of tissue specimens relative to the tissue mass or organ from which excised. This provides reliable and accurate assessment of margin status as well as a reproducible and accurate way to direct, if necessary, a surgical re-excision of an involved margin at the site of surgical excision. In addition, another embodiment of the present invention provides a mapping system wherein an excised tissue specimen can be sutured to, molded into, or otherwise attached thereto. Embodiments of the present invention provide a stable platform for pathologic sectioning. Additional embodiments allow the user to maintain a true, anatomically correct orientation between the operated breast and the tissue specimen.

In another embodiment, mapping materials for use at an operating table are provided. Such mapping materials include, but are not limited to, a breast map made of a suturable, absorbent material, color-coded sutures, and a detachable completed copy of an orientation map. The detachable completed copy of an orientation map may be kept in the patient's file, or otherwise attached to a permanent record.

It is generally understood by those of skill in the art that a pathologist must relay and preserve information regarding the position and orientation of the histological findings. This position and orientation information is typically communicated to the surgeon, particularly in cases where a cancerous tumor cancer has not been completely excised (e.g., where there are "close" or "dirty margins"). Such information is useful to the surgeon so that she may re-visit the surgical site in order to totally excise any remaining cancerous tissue.

In accordance with one embodiment of the present invention, mapping materials are supplied in a sterile outer package for use in the operating room. The outer packaging envelope will generally be resealable to prevent any contamination from within or without. In one embodiment, the envelope is opaque to assure confidential transport to either radiology or pathology.

In one embodiment, the packaged materials include a hard backed surface that is printed or impregnated with a map of the operated organ and a reference system. In one embodiment, the map contains geometrical and anatomical indices of distances, areas, and shapes apropos to the organ (e.g., the breast under investigation). The reference system permits precise anatomical positioning of excised tissue relative to its actual position and orientation in the operated organ. Either a graphic or physical representation of the tissue mass or organ can be used as the map. For example, the map can be printed from an imaging system or from a database with predefined organ maps. In another embodiment, the map is any other type of imprint or representation of the organ subject to the investigation. In one embodiment, indices to note right or left position are provided with the map. In another embodiment, an axillary map is provided for mapping in the event of sentinel node biopsy or axillary node dissection.

The backing material may be clipped to and/or suturable so that the excised specimen can be securely fixed thereto. The excised specimen may be attached to the map in the anatomical position and orientation that it had prior to excision. The backing material is absorbent in one embodiment, so that exuded tissue fluid can be captured, and if needed, preserved for future use. In one embodiment, the reverse side of the backing material/anatomical map includes a radio-opaque grid. In one embodiment, the radio-opaque grid corresponds to the anatomical map affixed to the front side of the backing material. In one embodiment, the radio-opaque grid is printed or impregnated thereon. The radio-opaque grid allows precise and accurate location of radio graphic abnormalities in relation to their true anatomic location in the excised specimen. This allows reliable, accurate, anatomically correct pathologic evaluation and provides the operating surgeon with definitive anatomical information if additional surgery is required. This also provides radiation oncologists with additional information in reference to the actual site or border of interest in the remaining organ.

In one embodiment, the backing material includes a material that is easily and cleanly cleaved with the specimen to avoid displacement from its true anatomic orientation vis-a-vis the excised specimen and in relation to its position relative to other tissue slices in the pathologic specimens. The backing material allows the specimen to be cut while joined to the map during histological examination, thus maintaining the original position and orientation of the excised specimen during the histological examination vis-à-vis itself. In one embodiment, the map material includes cardboard, sponge, plastic, foam (Styrofoam), or fabric.

In one embodiment the backing material is foldable. Foldability helps to minimize the packaging size. When used, the device can be unfolded, in order to provide maximum map area.

In another embodiment, staples and/or sutures (of differing colors) are provided. Multiple colors allow the surgeon to affix the specimen to the map face utilizing a coding system to facilitate its orientation at the operating room table. Colored inks may be provided so that the specimen, if desired, may be inked fully on all sides to facilitate pathologically oriented sectioning and assessment. A chart copy of the finished specimen orientation map is detachable for inclusion in the permanent patient record.

In one embodiment, a flexible ruler is included to measure actual distance of the excised specimen from designated tissue landmarks. For example, the tissue landmark may be the nipple areola skin junction. By measuring the distance of the excised specimen from the nipple areola skin junction, the volume of tissue requiring re-excision may be calculated. The ruler may provide centimeter, millimeter, or inch units, or any other unit as is known to those of skill in the art. In one embodiment, the ruler is self adhesive to facilitate attachment to the map.

A gross pathology breast map (GPBM) 10 in accordance with one embodiment of the present invention is illustrated in FIG. 1. The GPBM 10 of FIG. 1 includes several aligned layers 11, 12, 13, 14. Each layer accommodates different clinical needs. The layers may be combined together or used separately. The first layer 11 (e.g., the impregnated map layer 11) of the illustrated GPBM 10 is a graphic representation of the anatomy of the breast. In one embodiment, the graphic representation 11 is a geometrical representation where the nipple is clearly represented, as described in greater detail below. In another embodiment the graphic representation is anatomical, and includes other specific anatomic landmarks besides the nipple.

The relative position of excised tissue (not illustrated) to the anatomy may be uniquely identified by placing the excised tissue on the map 11 in its corresponding graphic location. After tissue has been excised from the breast and before it is placed on the map 11, the tissue may be painted with different colored ink to mark the anterior, posterior, superior, and inferior margins. The excised tissue is placed on the map 11 and it is sutured or otherwise fixed to the map in a geometrically representative position with respect to its original position within the breast.

In one embodiment, a backing material layer 12 is adapted to absorb body fluids and ensure stability for stitching or otherwise tacking the tissue to the map 11. Alternatively, in another embodiment, color-coded stitches are used to fixate the tissue to the map 11 and mark the anterior, posterior, superior, and inferior margins. The use of color-coded stitches eliminates the need for using ink to paint the tissue prior to placing it on the map 11. The map 11 with the affixed excised tissue is then placed in a sterile bag (not illustrated) and may be sent to a pathologist for histological examination or to radiology for x-ray imaging.

In one embodiment, a radio-opaque layer 13 of the GPBM 10 contains radio-opaque markers or elements that correspond to and are aligned relative to the graphic map representation layer 11. The radio-opaque markers allow for pathologic and histologic orientation of the abnormal area to its actual anatomic position in the operated organ.

A detachable layer 14 may be removed and archived for chart documentation purposes. In one embodiment, the detachable layer 14 includes a detachable chart copy. The detachable layer 14 may be used as a basis for further clinical treatment decisions. The detachable layer 14 contains a graphical representation of the organ aligned to the graphic map representation layer 11. When the detachable layer 14 is attached to the lower most layers, the surgeon may remove it prior to sending the remaining layers of the GPBM 10 to pathology or radiology.

The GPBM layers shown in FIG. 1 are representative but not limiting for the present invention. Several layers can be combined into one if appropriate for clinical and commercialization purposes. For example, in another embodiment, the graphic representation is printed directly on an absorbent cardboard or fabric, thereby effectively combining map layer 11 and backing material layer 12.

Figure 2:
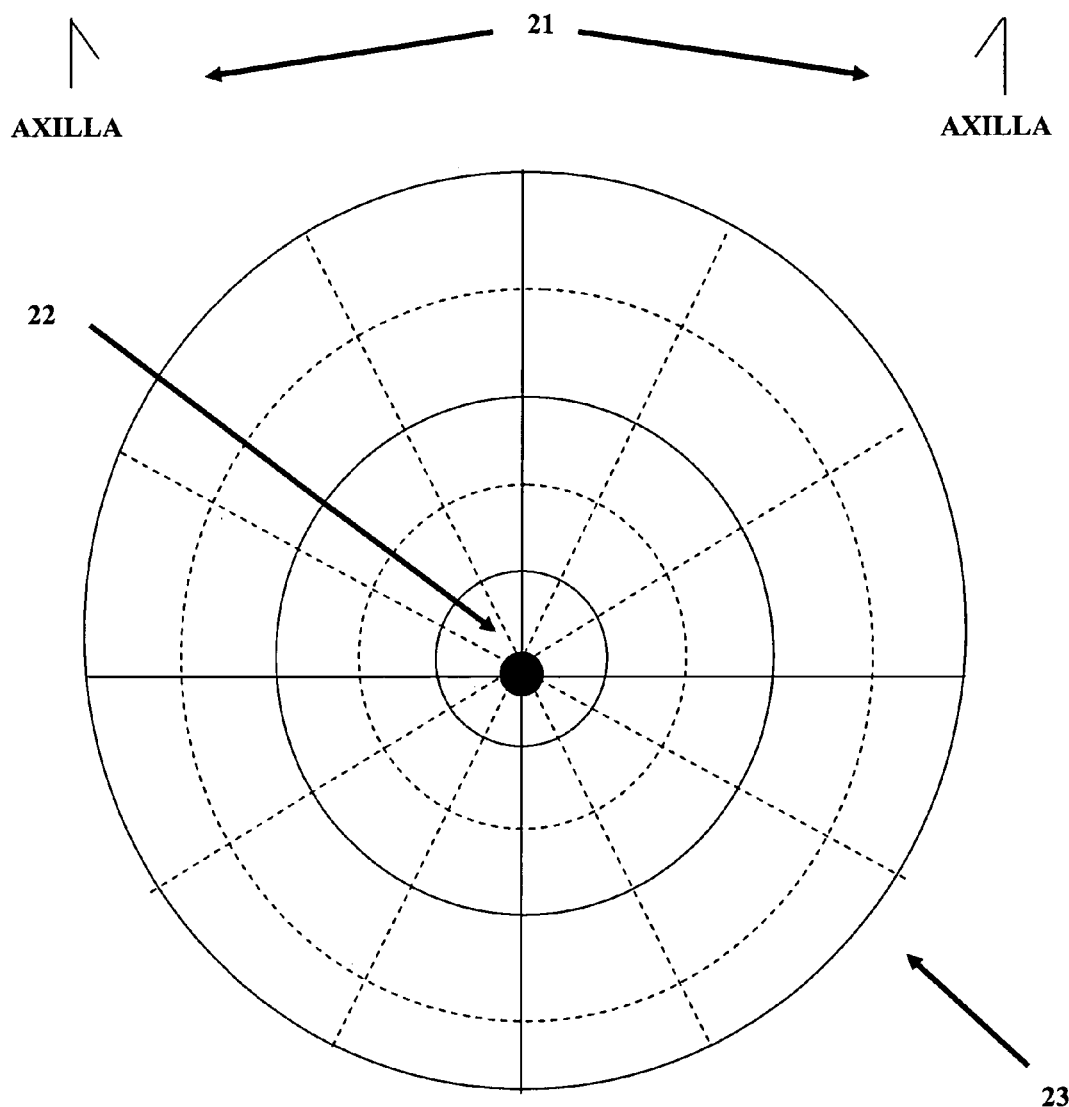
FIG. 2 illustrates one embodiment of a symmetrical breast map that includes a symmetrical graphical representation of a breast.
Figure 3:
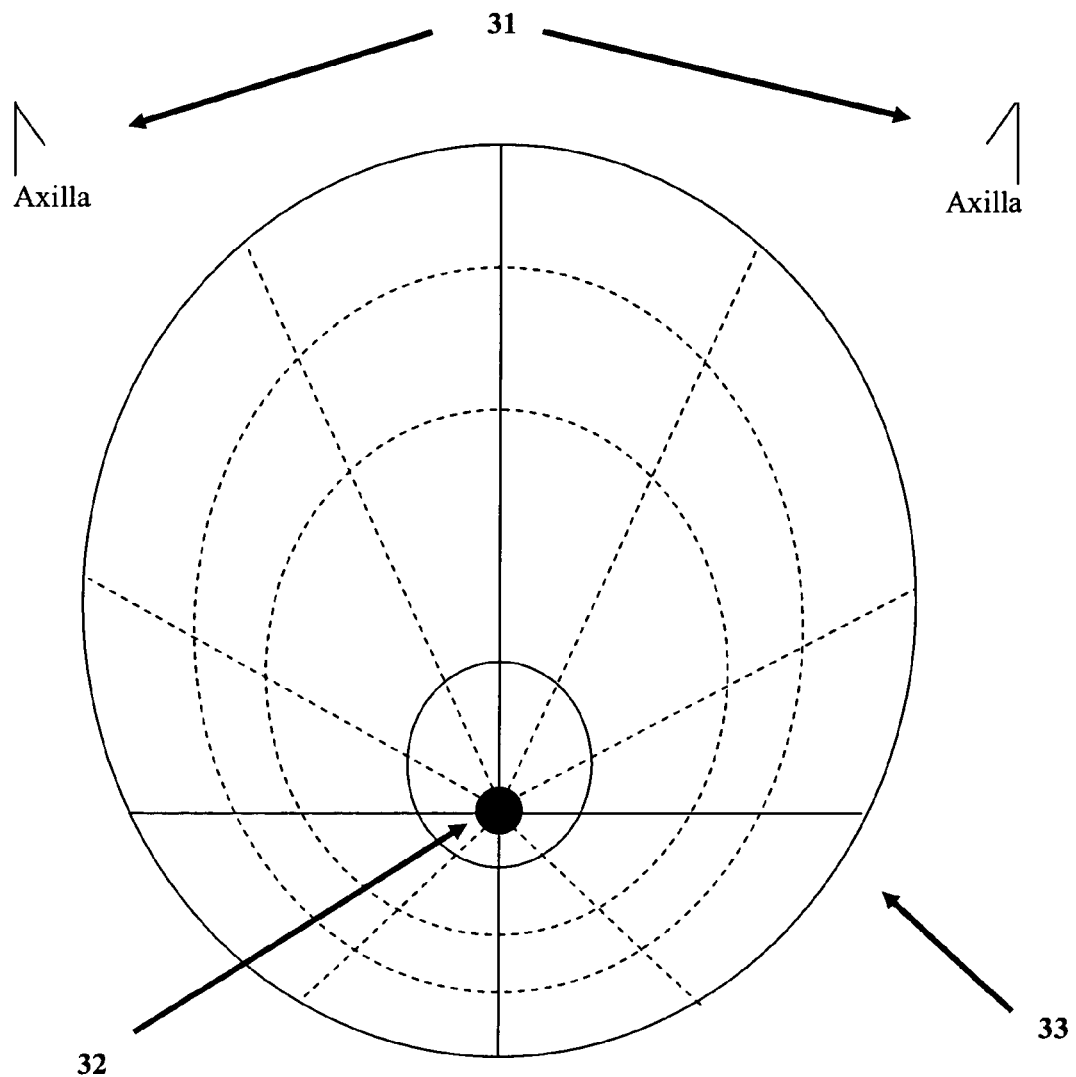
FIG. 3 illustrates one embodiment of an asymmetrical breast map that includes an asymmetrical graphical representation of a breast.
Figure 4:
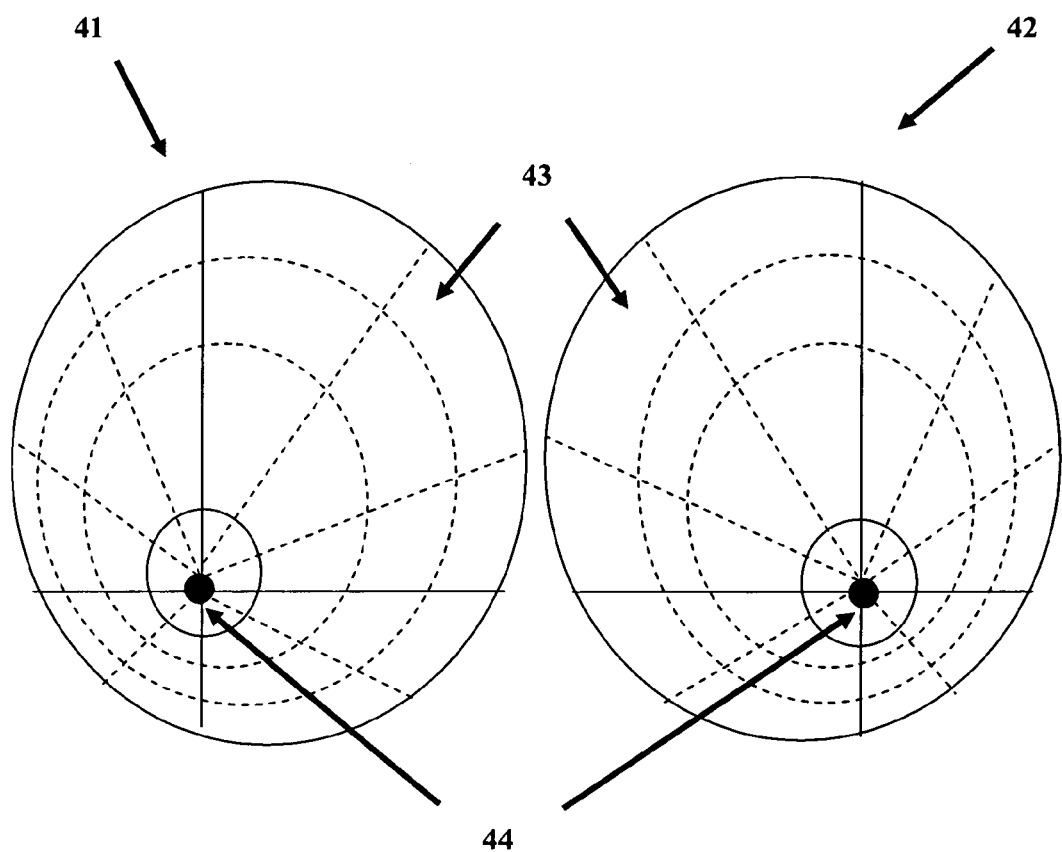
FIG. 4 illustrates one embodiment of a double breast map that includes a graphical representation of left and right breasts.

FIGS. 2, 3, and 4 illustrate different embodiments of graphical representations of the breast. These embodiments are representative only and shall not constitute a limitation of the present invention. Other representations of the breast may be used in order to serve as a graphic representation of the breast for the purpose of orienting and positioning an excised specimen. FIG. 2 shows a symmetrical, geometrical representation 23 of the breast. In one embodiment, the representation 23 is a graphical representation of an organ, and is geometrical and/or anatomical. The nipple is marked with nipple marker 22. Graphic representations of the axillae are provided by left and right axillae indicators 21. The axillae indicators 21 allow the surgeon to indicate the right or the left axilla on the map, thus identifying the operated side.

FIG. 3 illustrates an asymmetrical geometrical representation 33 of a breast. The representation 33 includes four breast quadrants. In one embodiment, the representation 33 includes a graphical representation of an organ, and is geometrical and/or anatomical. The nipple is marked with a nipple marker 32. Graphical representations of the axillae are provided with axillae markers 31 so that the surgeon can mark the right or the left axilla on the map and indicate the axillary level of operation as well. In one embodiment, the axillae markers 31 are indicators for the left and right axillae.

FIG. 4 shows one embodiment of a geometrical representation 43 of both breasts. In one embodiment, the geometrical representation 43 is a graphical representation of an organ, and is geometrical and/or anatomical. The right breast representation 41 and left breast representation 42 are shown with the nipples marked with nipple markers 44. In another embodiment, additional two- and three-dimensional graphic representations of the breast are used. For example, breast images obtained from imaging devices such as x-ray, magnetic resonance imaging (MRI), or ultrasound may be used as the representation 43.

Figure 5:
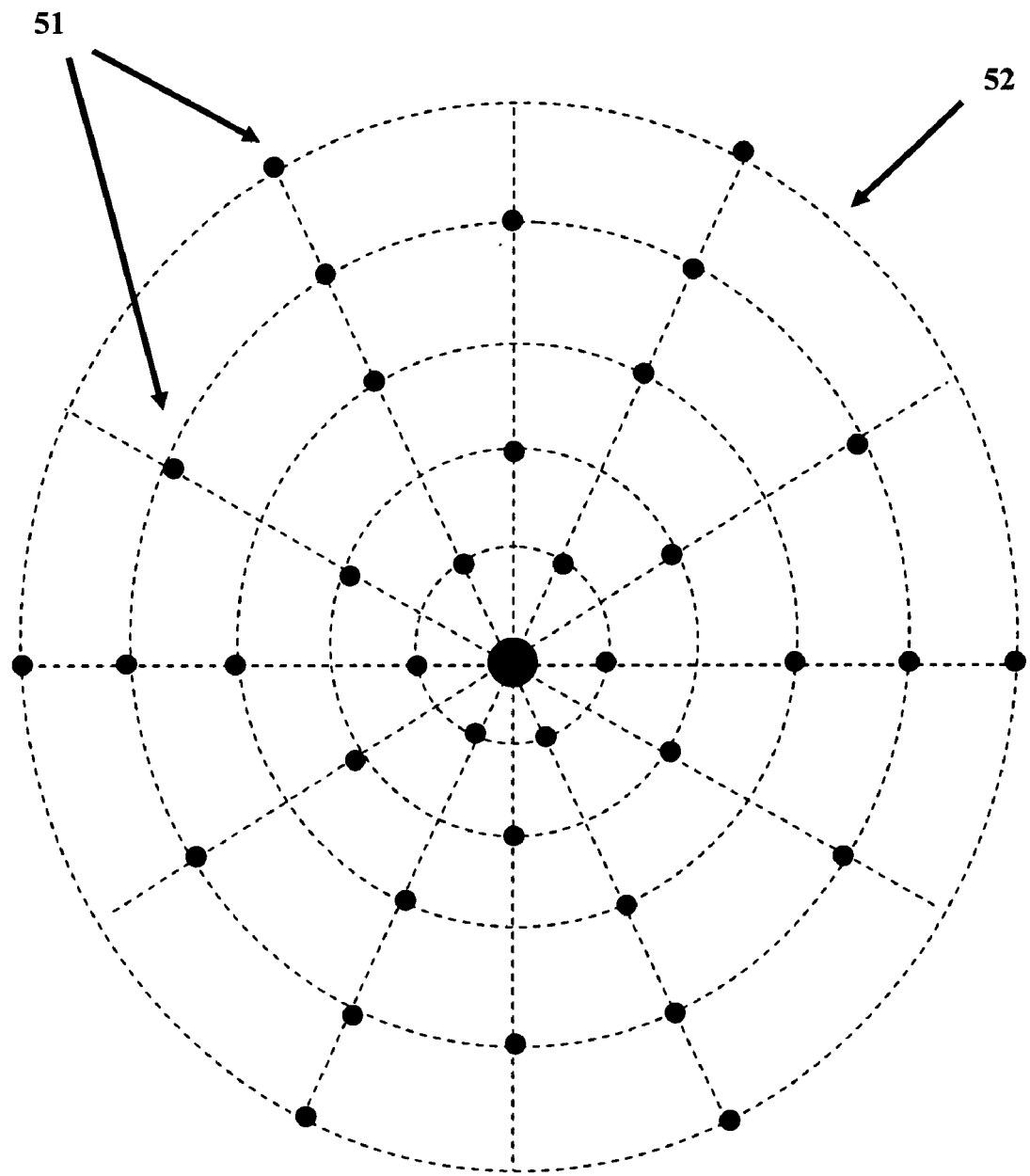
FIG. 5 illustrates one embodiment of a breast map that includes aligned placement of radio-opaque markers.

FIG. 5 illustrates one embodiment of a radio-opaque layer 52 that includes radio-opaque markers 51. In one embodiment, the radio-opaque layer includes an aligned graphical representation of an organ, and is geometrical and/or anatomical. The radio-opaque markers 51 are geometrically aligned with the symmetric graphic representation layer 23 of FIG. 2. The radio-opaque markers 51 are of such nature and design so that both the suturing of the specimen to the mapping device and pathologic specimen sectioning through this layer during pathologic analysis can be performed. Radio-opaque elements of representative shapes can be incorporated into or glued or otherwise attached to the backing material layer (not shown).

In one embodiment of the GPBM device, the backing material will be folded in order to minimize packaging size. When used, the device can be unfolded in order to provide maximum map area.

In another embodiment of the present invention, a GPBM device is provided in a sterile bag together with other materials that may be required by the particular surgical procedure. These additional materials, listed below, are representative and should not constitute a limitation of the invention. In one embodiment, the additional materials include: a) ink; b) pens; c) stitches, which in one embodiment are color-coded; d) staples or clips, which in one embodiment are color-coded; and e) a ruler, which in one embodiment is a flexible centimeter ruler, which may be self-adhesive.

Figure 6:
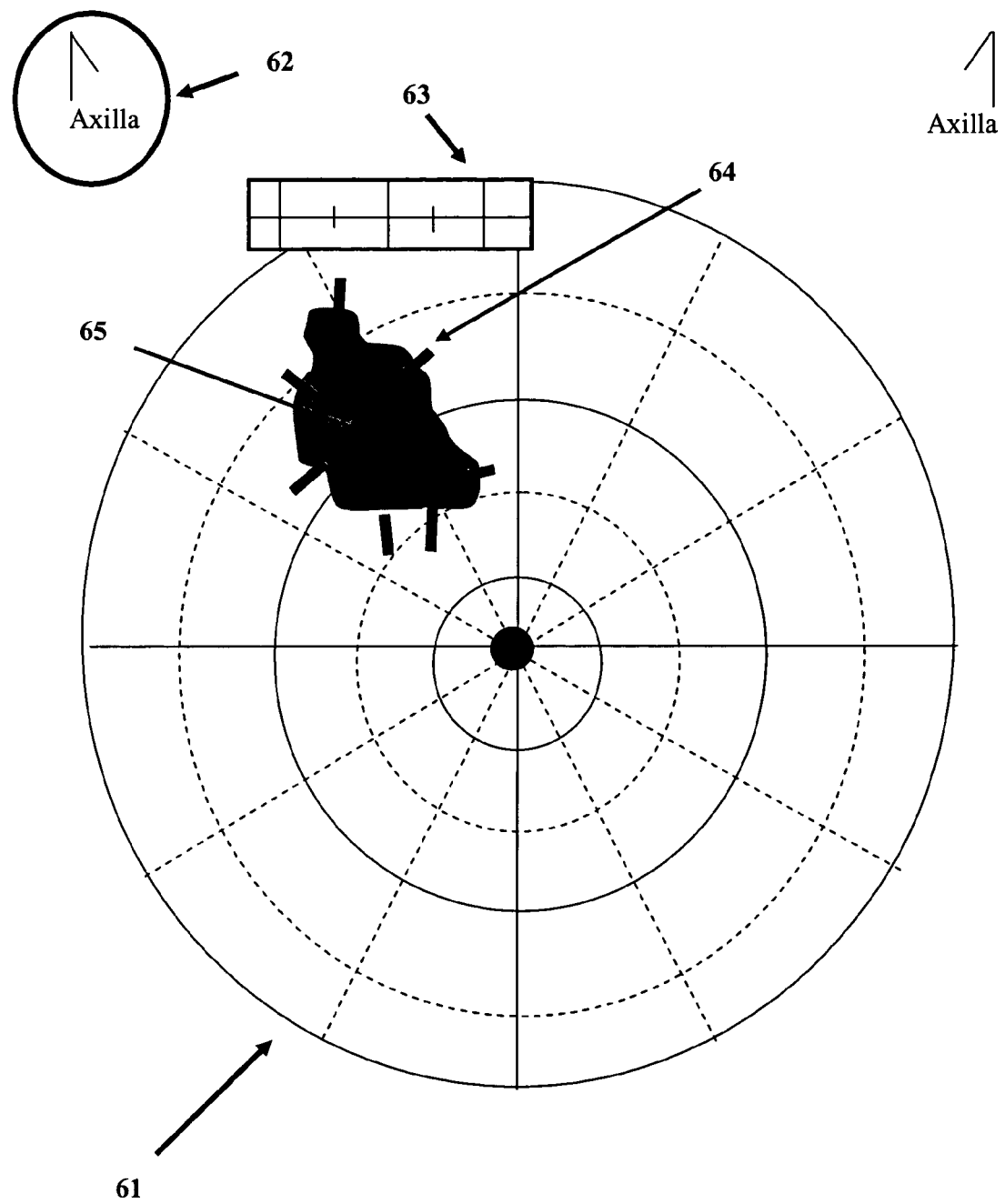
FIG. 6 illustrates one embodiment of a breast map that includes an excised specimen attached thereto.

FIG. 6 illustrates an excised specimen 65 placed on the GPBM device 61. One of the axillae 62 has been marked by the surgeon in order to indicate the right breast. The specimen 65 has been attached to the GPBM device 61 by using stitches 64, although it is understood that clips, adhesives, tacks, or other bonding materials as are well known to those of skill in the art may be used. In one embodiment, color coded stitches or clips 64 are used to mark the specimen 65 orientation. A piece of flexible ruler 63, such as a centimeter ruler, is placed on the GPBM device 61 as a distance marker. In a preferred embodiment, the flexible centimeter ruler is self-adhesive.

Any of the embodiments of the GPBM device may be packaged in a sterile container and available on request in the operating room after any type of surgical excision. In one embodiment, the materials included in the sterile container are utilized at the operating room table by the surgeon. The excised specimen is placed on the GPBM in the correct anatomical position and alignment as determined by the surgical excisional site in the operated breast. In one embodiment, the specimen is fixed to the map by sutures, staples, or other devices. The specimen may be inked by applying different colored inks to the specimen's various surfaces.

The map with affixed specimen is then placed into its sterile opaque sealed container. The container is removed from the surgical table and sent for radiologic assessment and then to pathology for histologic examination. In one embodiment, the container is sent directly to pathology. In either case, the pathologist will have precise anatomic indices of the location of the abnormality in relation to the specimen as well as the orientation of the specimen to the surgical site of excision.

Pathologic sectioning may be performed through the backing material. The backing material provides a stable platform for this sectioning step. The backing material also allows the excised tissue to be reconstituted in its original form, thereby maintaining all anatomic relationships. Any requirement for additional tissue excision as determined pathologically may then be anatomically precisely identified in the specimen and correlated by the surgeon to its exact anatomical site in the operated breast.

The present invention has been described in terms of certain specific embodiments. However, changes and variations on the foregoing will become apparent to those of skill in the art in view of the disclosure herein. Accordingly, the invention is not intended to be limited by the foregoing embodiments, but rather by the full scope of the attached claims.

What is claimed is:

1. A gross pathology breast map system for examining a breast tissue specimen while recording and maintaining an anatomical location of the specimen to a breast from which it was excised, the system comprising:
   a. a top layer comprising a substantially hard, suturable, tackable material, and a graphic representation of a breast anatomy, said graphic representation illustrating:
      i. a nipple located inside an outline of the breast;
      ii. an axilla; and
      iii. an alpha-numeric background grid to define a location of the specimen on the gross pathology breast map system; and
   b. a second layer affixed and aligned to the top layer, wherein said second layer is made of an absorptive, suturable, tackable material, said second layer comprising a back surface, wherein said back surface comprises radio-opaque elements that correspond to the graphic representation of the top layer.

2. A gross pathology breast map system for examining a breast tissue specimen while recording and maintaining an anatomical location of the specimen to the breast from which it was excised, the system comprising:
   a. a top layer made of a substantially hard, suturable, tackable material, said top layer comprising a graphic representation of a breast anatomy, said graphic representation showing a nipple located inside an outline of the breast, an axilla, and an alpha-numeric background grid to define a location of the specimen on the map;
   b. a second layer affixed and aligned to the top layer, said second layer comprising an absorptive, suturable, tackable material; and
   c. a third layer affixed to and aligned with the second layer, said third layer comprising radio-opaque markers that correspond to the graphic representation of the top layer.

3. A method for radiographically and histologically examining a breast tissue specimen while recording and maintaining the an anatomical location of the specimen to the breast from which it was excised, the method comprising:
   a. excising a tissue specimen from a breast location in a breast;
   b. affixing the tissue specimen on a gross pathology breast map that includes a graphic representation of a breast anatomy including a nipple location, in a map location that is substantially the same as the breast location;
   c. placing the gross pathology breast map with affixed specimen into a leakproof, resealable container;
   d. taking a radiographic image of the specimen; and
   e. submitting the gross pathology breast map with affixed specimen for pathologic sectioning.

4. A gross pathology breast map system for examining a breast tissue specimen while recording and maintaining the an anatomical location of the specimen to the breast from which it was excised, the system comprising:
   a. a top layer made of a substantially hard, suturable, tackable material, said top layer having a graphic representation of a breast anatomy, said graphic representation showing a nipple located inside an outline of the breast, an axilla, and an alpha-numeric background grid to define a location of the specimen on the map.
   b. a second layer affixed and aligned to the top layer, said second layer comprising an absorptive, suturable, tackable material, wherein the second layer further comprises a back surface, wherein said back surface comprises radio-opaque markers that correspond to the graphic representation of the top layer; and
   c. a third, detachable, radiosensitive bottom layer affixed and aligned to the second layer, said third layer comprising a second graphical representation of the breast aligned to the graphic representation of the top layer.

5. A method for radiographically and histologically examining a breast tissue specimen while recording and maintaining an anatomical location of the specimen to the breast from which it was excised, the method comprising:
   a. excising a tissue specimen from a breast location in a breast of a patient;
   b. identifying margins of the tissue specimen;
   c. affixing the tissue specimen on a gross pathology breast map in a representative location that is substantially representative of the breast location;
   d. placing the gross pathology breast map with affixed specimen into a leakproof, resealable container;
   e. taking a radiographic image of the specimen;
   f. removing a radiosensitive back layer from the gross pathology breast map and including it in a patient's chart; and
   g. providing the gross pathology breast map with affixed specimen for pathologic sectioning.

* * * * *